US00PP26024P3

(12) United States Plant Patent
Nir

(10) Patent No.: US PP26,024 P3
(45) Date of Patent: Oct. 27, 2015

(54) ***CHAMELAUCIUM* PLANT NAMED 'ROTEMWAX'**

(50) Latin Name: *Chamelaucium uncinatum*
Varietal Denomination: ROTEMWAX

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 113 days.

(21) Appl. No.: 13/986,492

(22) Filed: May 7, 2013

(65) Prior Publication Data

US 2014/0338079 P1 Nov. 13, 2014

(51) Int. Cl.
*A01H 5/02* (2006.01)

(52) U.S. Cl.
USPC ..... Plt./229
CPC ..... *A01H 5/02* (2013.01)

(58) Field of Classification Search
USPC ..... Plt./229
CPC ..... A01H 5/00
See application file for complete search history.

(56) References Cited

PUBLICATIONS

Nir Nursery (obtained from internet Sep. 18, 2014).*
UPOV Record Detail (obtained from UPOV website Sep. 18, 2014).*

* cited by examiner

*Primary Examiner* — Keith Robinson
(74) *Attorney, Agent, or Firm* — Cassandra Bright

(57) ABSTRACT

A new and distinct *Chamelaucium* cultivar named 'ROTEMWAX' is disclosed, characterized by a unique deep pink color throughout the flower. The new variety is early blooming and is very well branched. The new variety is a *Chamelaucium*, normally producing cut flower stems, or as a garden or container plant.

1 Drawing Sheet

Latin name of the genus and species: *Chamelaucium uncinatum.*

Variety denomination: 'ROTEMWAX'.

BACKGROUND OF THE INVENTION

The new *Chamelaucium* cultivar is a product of a planned breeding program conducted by the inventor, Nitzan Nir, in Kfar Hess, Israel. The objective of the breeding program was to produce new *Chamelaucium* varieties for ornamental commercial applications. The new variety was selected as a hybrid seedling from the breeding program at a commercial nursery in Kfar Hess, Israel.

The seed parent is the unpatented variety referred to as *Chamelaucium uncinatum* 'M.B.Violet' The pollen parent is the unpatented variety referred to as *Chamelaucium uncinatum* 'M.B. Orchid'. The new variety was discovered in December of 2008 by the inventor in a group of seedlings resulting from the previously mentioned crossing in a commercial nursery in Kfar Hess, Israel.

Asexual reproduction of the new cultivar has been performed by vegetative cuttings. This was first performed at a commercial nursery in Kfar Hess, Israel in November of 2009 and has shown that the unique features of this cultivar are stable and reproduced true to type in successive generations.

SUMMARY OF THE INVENTION

The cultivar 'ROTEMWAX' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ROTEMWAX'. These characteristics in combination distinguish 'ROTEMWAX' as a new and distinct *Chamelaucium* cultivar:

1. Early blooming season.
2. Unique deep pink flower throughout flower.
3. Medium flower size.
4. Large quantity of flowers.
5. Well branched plants.

PARENT COMPARISON

Plants of the new cultivar 'ROTEMWAX' are similar to plants of the seed parent, *Chamelaucium uncinatum* 'M.B. Violet' in most horticultural characteristics, however, plants of the new cultivar 'ROTEMWAX' produce flowers of a darker pink, at an earlier bloom date than the seed parent. 'ROTEMWAX' also produces a more branched habit and more flowers compared to the seed parent.

Plants of the new cultivar 'ROTEMWAX' are similar to plants of the pollen parent; *Chamelaucium uncinatum* 'M.B. Orchid' in most horticultural characteristics, however, plants of the new cultivar 'ROTEMWAX' produce flowers of a much darker pink color, at an earlier bloom date than the pollen parent.

COMMERCIAL COMPARISON

Plants of the new cultivar 'ROTEMWAX' are comparable to the variety *Chamelaucium uncinatum* 'Eden', unpatented. The two *Chamelaucium* varieties are similar in most horticultural characteristics; however, the new variety 'ROTEMWAX' produces flowers with a more deep pink color, whereas flowers of 'Eden' are a deeper purple color. Additionally, plants of 'ROTEMWAX' produce more flowers and buds per plant. Plants of 'ROTEMWAX' are better branched than plants of 'Eden' and produce flowers earlier in the season.

Plants of the new cultivar 'ROTEMWAX' can also be compared to the commercial variety *Chamelaucium uncinatum* 'Early Violet', unpatented. These varieties are similar in most horticultural characteristics; however plants of 'ROTEMWAX' branch better and produce flowers that are pink throughout, whereas flower of 'Early Violet' have a white ring in the center.

BRIEF DESCRIPTION OF THE PHOTOGRAPH

The accompanying photograph in FIG. 1 illustrates in full color a close up of typical flowers and foliage of 'ROTEMWAX' at approximately 1 year of age.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'ROTEMWAX' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'ROTEMWAX'.

Age of plant described: At least 2 months old from a rooted cutting.

Typical flowering stems harvested per plant: 120 to 150 during the course of the season.

Vase life of flowers: Two weeks.

PROPAGATION

Time to produce a rooted plantlet: 30 to 60 days at approximately 24° C.

Root description: Fibrous.

PLANT

Growth habit: Upright plant produces multiple stems from a pinch, or after harvesting stems.

Height: 200 cm.

Plant spread: 80 cm.

Growth rate: Rapid.

Branching characteristics: Excellent branching occurs after pinching.

Length of primary lateral branches: 60 cm on average.

Diameter of lateral branches: 0.5 cm.

Quantity of primary lateral branches: 120. These are the harvested flowering stems.

Characteristics of primary lateral branches:

- *Form*.—Round.
- *Diameter*.—0.5 cm.
- *Color*.—Near RHS Yellow-Green 147A.
- *Texture*.—Smooth.
- *Strength*.—Stems brittle.

Internode length: Range from 1.5 to 11 cm.

FOLIAGE

Leaf:

- *Arrangement*.—Opposite.
- *Quantity*.—Approximately 6 leaves, in the 10-15 cm section from the top of the branch.
- *Average length*.—1.8 cm.
- *Average width*.—0.1 cm.
- *Shape of blade*.—Needle.
- *Apex*.—Acute.
- *Base*.—Attenuate.
- *Margin*.—Entire.
- *Texture*.—Glabrous all surfaces.
- *Pubescence*.—None.
- *Aspect*.—Straight, occurring at approximately a 15 to 45 degree angle.
- *Color*.—Young foliage: Near RHS Yellow-Green 147B. Mature foliage: Near RHS Green 137A.
- *Venation*.—Indistinguishable from foliage.
- *Petiole*.—Not present.

FLOWER

Natural flowering season: Plants planted during April through October begin flowering December through February, without a juvenility period in Kfar Hess, Israel. Plants flower continuously under short day conditions.

Days to flowering from rooted cutting: Approximately 60 days.

Inflorescence type: Terminal Panicle.

Individual flower type: Single, rotate 5 petaled with a cone shaped hypanthium. Flowers outwardly facing.

Persistent or self-cleaning: Self-Cleaning.

Lastingness: Up to 14 days in a vase. Approximately 45 to 60 days on the plant.

Typical flowering stem length: Approximately 75 cm.

Bud:

- *Shape*.—Spherical.
- *Length*.—0.45 cm.
- *Diameter*.—0.45 cm.
- *Color*.—Near RHS Red-Purple 59A.

Inflorescence size:

- *Diameter*.—Average 26 cm.
- *Length*.—Average 20 cm.

Flower size:

- *Diameter*.—Average 1.5 cm.
- *Length*.—Average 0.6 cm.

Corolla:

- *Petals*.—Arrangement: Rotate, not overlapping. Length: Average 0.5 cm. Diameter: Average 0.5 cm. Quantity: 5. Texture: smooth. Apex: Obtuse rounded. Base: Fused into a hypanthium.
- *Color*.—When opening: Upper surface: Near RHS Purple 72A. Lower surface: Near RHS Purple 72A. Fully opened: Upper surface: Near RHS Purple 72A. Lower surface: Near RHS Purple 72A. Aging: Upper surface: Near RHS Purple 72B. Lower surface: Near RHS Purple 72B.

Hypanthium:

- *Diameter*.—Average 0.8 cm.
- *Length*.—Average 0.3 cm.
- *Shape*.—Obconical.
- *Color*.—When opening: Upper surface: Near RHS Purple 72A. Lower surface: Near RHS Purple 72A. Fully opened: Upper surface: Near RHS Purple 72A.

Lower surface: Near RHS Purple 72A. Aging: Upper surface: Near RHS Purple 72B. Lower surface: Near RHS Purple 72B.

Calyx/sepals:

*Quantity per flower*.—Fused into a single, conical structure.

*Length*.—0.3 cm.

*Width*.—0.8 cm.

*Margin*.—Entire, incised approximately 3 mm.

*Texture*.—Smooth.

*Color*.—Near RHS Green 137A, background color, covered almost entirely with Greyed-Purple N186D.

Peduncle: Peduncle consists of the plant stem.

Pedicel:

*Length*.—0.8 cm.

*Diameter*.—0.1 cm.

Fragrance: None.

REPRODUCTIVE ORGANS

Stamens:

*Number*.—10.

*Filament length*.—1 mm.

*Filament color*.—Near RHS Red-Purple 63A.

Anthers:

*Shape*.—Oval.

*Length*.—0.25-0.5 mm.

*Width*.—0.2 mm.

*Color*.—Near RHS Purple 75C.

Pollen: Not observed to date.

Pistil:

*Number*.—1.

*Length*.—0.5 cm.

*Color*.—Near RHS White 155A.

*Style color*.—Near RHS Red-Purple N74C.

*Stigma*.—Shape: Round. Color: Near RHS Purple 75A. Texture: Glabrous.

OTHER CHARACTERISTICS

Seeds and fruits: Single flower produces one fruit. When the fruit is fertile, it will produce 1 seed, occasionally 2 seeds. Fruit type is a nut, colored near Grey-Brown N199A, seed is unwinged colored approximately 1.5 mm, brown in color, too minute to accurately measure color with RHS chart.

Disease/pest resistance: Neither resistance nor susceptibility to the normal diseases and pests of *Chamelaucium* have been observed to date.

Temperature tolerance: From −2° C. to 35° C.

Drought tolerance: Very good tolerance for drought.

What is claimed is:

1. A new and distinct cultivar of *Chamelaucium* plant named ‘ROTEMWAX’ as herein illustrated and described.

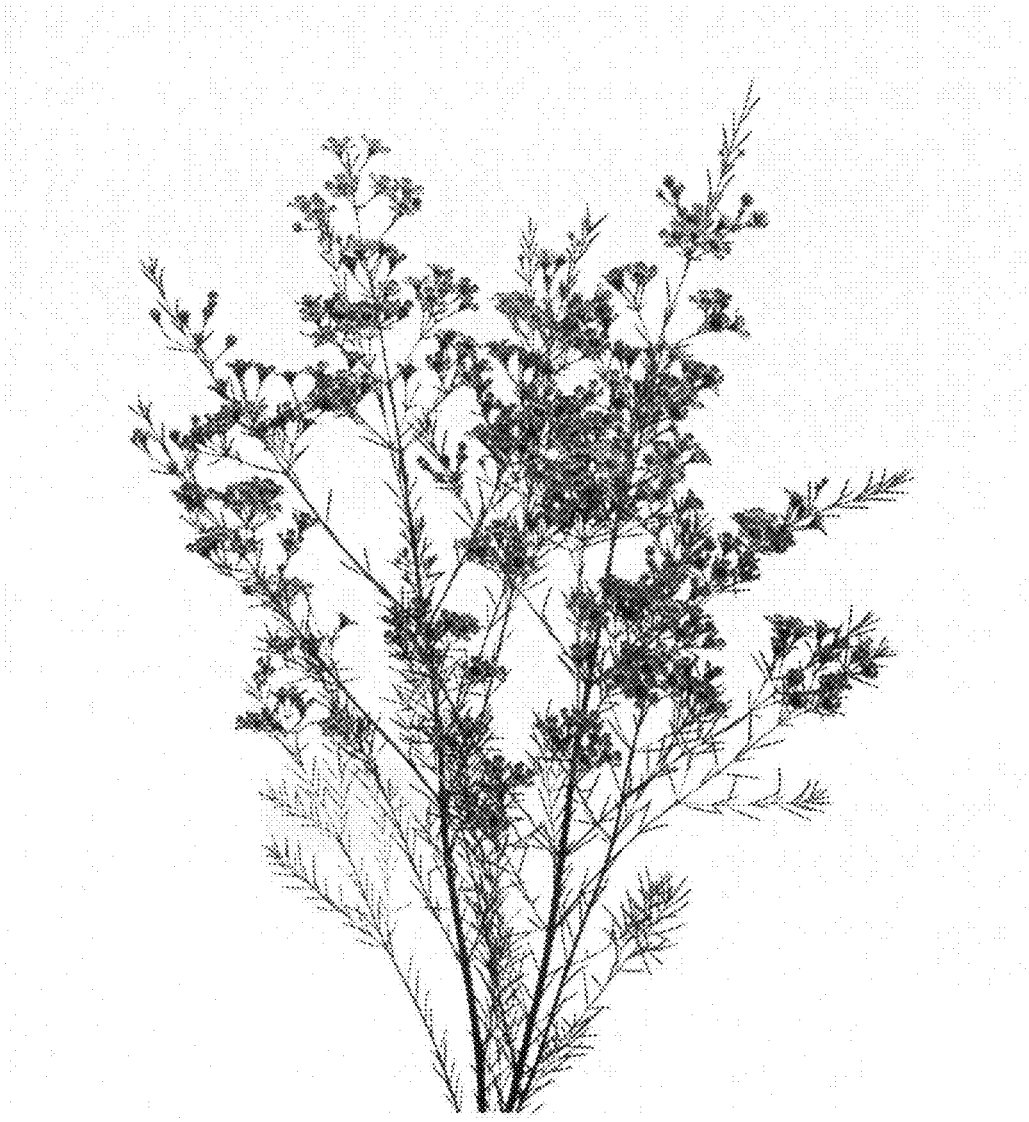

* * * * *